(12) United States Patent
Ward

(10) Patent No.: US 8,309,025 B1
(45) Date of Patent: Nov. 13, 2012

(54) METHODS AND SYSTEMS FOR DETERMINING COMPOSITION AND COMPLETION OF AN EXPERIMENT

(75) Inventor: Allen G. Ward, Austin, TX (US)

(73) Assignee: Luminex Corporation, Austin, TX (US)

( * ) Notice: Subject to any disclaimer, the term of this patent is extended or adjusted under 35 U.S.C. 154(b) by 1335 days.

(21) Appl. No.: 11/627,473

(22) Filed: Jan. 26, 2007

Related U.S. Application Data

(60) Provisional application No. 60/762,545, filed on Jan. 26, 2006.

(51) Int. Cl.
*G01N 33/48* (2006.01)

(52) U.S. Cl. ............. 422/62; 422/50; 422/63; 422/68.1; 436/43; 436/50; 436/55; 436/63

(58) Field of Classification Search ............. 422/50, 422/62, 63, 68.1; 436/43, 50, 55, 63
See application file for complete search history.

(56) References Cited

U.S. PATENT DOCUMENTS

| | | | |
|---|---|---|---|
| 5,736,330 A | 4/1998 | Fulton | |
| 5,981,180 A | 11/1999 | Chandler et al. | |
| 6,046,807 A | 4/2000 | Chandler | |
| 6,057,107 A | 5/2000 | Fulton | |
| 6,139,800 A | 10/2000 | Chandler | |
| 6,268,222 B1 | 7/2001 | Chandler et al. | |
| 6,366,354 B1 | 4/2002 | Chandler | |
| 6,411,904 B1 | 6/2002 | Chandler | |
| 6,449,562 B1 | 9/2002 | Chandler et al. | |
| 6,514,295 B1 | 2/2003 | Chandler et al. | |
| 6,524,793 B1 | 2/2003 | Chandler et al. | |
| 6,528,165 B2 | 3/2003 | Chandler | |
| 6,592,822 B1 | 7/2003 | Chandler | |
| 6,649,414 B1 | 11/2003 | Chandler et al. | |
| 6,939,720 B2 | 9/2005 | Chandler et al. | |
| 2006/0105395 A1 | 5/2006 | Pempsell | |

OTHER PUBLICATIONS

U.S. Appl. No. 60/732,535 entitled "Methods and Systems for Automatically Determining Assay Type," filed Nov. 2, 2005.

*Primary Examiner* — Lyle Alexander
(74) *Attorney, Agent, or Firm* — Fulbright & Jaworski L.L.P.

(57) ABSTRACT

Methods and systems for determining composition and completion of an experiment are provided. One-computer-implemented method for determining composition and completion of an experiment includes determining one or more characteristics of data acquired during the experiment and determining if the experiment is completed based on the one or more characteristics. One system configured to determine composition and completion of an experiment includes a processor configured to determine one or more characteristics of data acquired during the experiment and to determine if the experiment is completed based on the one or more characteristics. Another system configured to perform an experiment includes a measurement subsystem configured to acquire data during the experiment and a processor configured to determine one or more characteristics of the data during the experiment and to determine the composition of the experiment and if the experiment is completed based on the one or more characteristics.

6 Claims, 4 Drawing Sheets

METHODS AND SYSTEMS FOR DETERMINING COMPOSITION AND COMPLETION OF AN EXPERIMENT

PRIORITY CLAIM

The present application claims priority to U.S. Provisional Application No. 60/762,545 filed Jan. 26, 2006.

BACKGROUND OF THE INVENTION

1. Field of the Invention

This invention generally relates to methods and systems for determining composition and completion of an experiment. Certain embodiments relate to methods and systems for determining composition and completion of an experiment based on one or more characteristics of data acquired during the experiment.

2. Description of the Related Art

The following descriptions and examples are not admitted to be prior art by virtue of their inclusion within this section.

Generally, flow cytometers are used to perform measurements of fluorescence intensity of laser excited polystyrene beads or cells as they pass linearly through a flow chamber. However, flow cytometers can also be used to perform measurements of one or more properties of other particles. Some systems are configured to perform measurements of the level of light scattered by particles at 90° or 180° to the excitation source, two or more measurements of fluorescence used to determine classification, which is the particle "identity," and additional fluorescence measurements known as "reporters," typically used to quantify chemical reactions of interest. Each of the fluorescent measurements is made at a different wavelength or waveband of emission.

As the measurement capability of flow cytometer type measurement instruments has improved, the applications in which flow cytometers can be used to perform measurements has increased drastically. For example, flow cytometers have become increasingly useful in providing data for applications such as biological assays (e.g., displacement or competitive assays, non-competitive assays, enzyme assays), nucleic acid analysis, and combinatorial chemistry. In particular, the popularity of flow cytometer measurements has dramatically increased due to the speed with which assays can be performed by flow cytometers particularly in comparison to other assay methods (e.g., conventional enzyme linked immunosorbent assay "ELISA" format).

Imaging using detectors such as charged coupled device (CCD) detectors is also employed in several currently available instruments for biotechnology applications. Many of the commercially available systems are configured to image human (or other animal) cells. Such systems are not configured to generate images at different wavelengths or wavebands of fluorescence emission such that the images could be used to determine the identity of the cells or subset to which the cells belong. Instead, for multiplexed applications in which CCD detectors are used to measure fluorescent emission of cells, the subset or class of cells or other particles is determined based on the absolute position of the fluorescence emission within the image rather than the characteristics of the fluorescence emission such as wavelength composition.

When performing multiple assay tests simultaneously (i.e., in a single experiment), it is often necessary to indicate the tests (e.g., particle "identities," fluorescence spectral addresses, position of fluorescence emissions, etc.) included in the experiment before the experiment begins and to define experiment parameters that can be used to determine when the experiment is complete. Selecting the various tests that are included in a particular experiment, from all of the possible tests that could be included in a multiplex test experiment, is time consuming, can lead to errors, and obligates the user to know ahead of time which tests are included. In addition, users of multiplex systems sometimes use different tests for different samples within a single experiment. In this manner, users are required to: 1) identify all of the tests included in the entire experiment for all of the samples regardless of which subsets of tests are used for particular samples; and 2) designate a "total count" threshold so that data acquired for each test is permitted to be recorded regardless of whether the tests are used for each sample. These requirements for the user are disadvantageous for at least the reasons set forth above.

Accordingly, it would be desirable to develop methods and systems for determining composition and completion of an experiment such that the need to indicate the individual tests included in the experiment before the experiment and to supply parameters that indicate when the experiment is completed are eliminated.

SUMMARY OF THE INVENTION

The following description of various embodiments of methods, carrier media, and systems is not to be construed in any way as limiting the subject matter of the appended claims.

One embodiment relates to a computer-implemented method for determining composition and completion of an experiment. The method includes determining one or more characteristics of data acquired during the experiment. The method also includes determining if the experiment is completed based on the one or more characteristics. These steps may be performed as described further herein. In addition, this embodiment of the method may include any other step(s) of any other method(s) described herein.

Another embodiment relates to a carrier medium that includes program instructions executable on a computer system for performing a computer-implemented method for determining composition and completion of an experiment. The computer-implemented method includes determining one or more characteristics of data acquired during the experiment. The method also includes determining if the experiment is completed based on the one or more characteristics. These steps may be performed as described further herein. In addition, the computer-implemented method for which the program instructions are executable may include any other step(s) of any other method(s) described herein. The embodiment of the carrier medium described above may be further configured as described herein.

An additional embodiment relates to a system configured to determine composition and completion of an experiment. The system includes a processor configured to determine one or more characteristics of data acquired during the experiment and to determine if the experiment is completed based on the one or more characteristics. The processor may be configured to determine the one or more characteristics and to determine if the experiment is completed as described further herein. The processor and the system may be further configured as described herein.

A further embodiment relates to a system configured to perform an experiment. The system includes a measurement subsystem configured to acquire data during the experiment. The measurement system may be configured to acquire the data as described further herein. The system also includes a processor configured to determine one or more characteristics of the data during the experiment and to determine the composition of the experiment and if the experiment is completed based on the one or more characteristics. The processor may be configured to determine the one or more characteristics and to determine the composition of the experiment and if the experiment is completed based on the one or more characteristics as described further herein. The measurement subsystem, the processor, and the system may be further configured as described herein.

BRIEF DESCRIPTION OF THE DRAWINGS

Other objects and advantages of the invention will become apparent upon reading the following detailed description and upon reference to the accompanying drawings in which.

Figure 1:
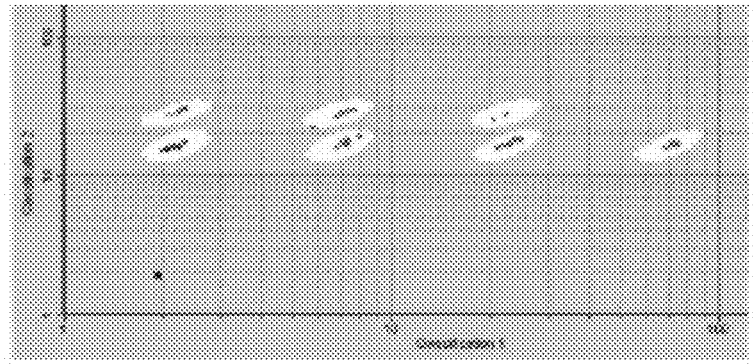
FIGS. 1-5 are representative graphical displays of five different time points during a simulated experiment at which a characteristic of the experiment is determined.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Although embodiments are described herein with respect to particles and microspheres, it is to be understood that the systems and methods described herein may also be used with microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substances known in the art. The particles may serve as vehicles for molecular reactions. Examples of appropriate particles are illustrated in U.S. Pat. Nos. 5,736,330 to Fulton, 5,981,180 to Chandler et al., 6,057,107 to Fulton, 6,268,222 to Chandler et al., 6,449,562 to Chandler et al., 6,514,295 to Chandler et al., 6,524,793 to Chandler et al., and 6,528,165 to Chandler, which are incorporated by reference as if fully set forth herein. The systems and methods described herein may be used with any of the particles described in these patents. In addition, particles for use in method and system embodiments described herein may be obtained from manufacturers such as Luminex Corporation, Austin, Tex. The terms "particles" and "microspheres" are used interchangeably herein.

In addition, the types of particles that are compatible with the systems and methods described herein include particles with fluorescent materials attached to, or associated with, the surface of the particles. These types of particles, in which fluorescent dyes or fluorescent particles are coupled directly to the surface of the particles in order to provide the classification fluorescence (i.e., fluorescence emission measured and used for determining an identity of a particle or the subset to which a particle belongs), are illustrated in U.S. Pat. Nos. 6,268,222 to Chandler et al. and 6,649,414 to Chandler et al., which are incorporated by reference as if fully set forth herein. The types of particles that can be used in the methods and systems described herein also include particles having one or more fluorochromes or fluorescent dyes incorporated into the core of the particles. Particles that can be used in the methods and systems described herein further include particles that in of themselves exhibit one or more fluorescent signals upon exposure to one or more appropriate light sources. Furthermore, particles may be manufactured such that upon excitation the particles exhibit multiple fluorescent signals, each of which may be used separately or in combination to determine an identity of the particles.

Embodiments described herein generally relate to determining composition and completion of an experiment. The embodiments also generally relate to aspects of multiplex testing and systems and defining which tests (e.g., particle "identities," fluorescence spectral addresses, position of fluorescence emissions, etc.) are included in an experiment performed by the multiplex system. The embodiments further generally relate to defining thresholds that can be used to determine when an experiment is completed. In addition, the embodiments described herein can be used to eliminate the requirement for having a user indicate a subset of tests included in an experiment from all possible tests capable of being examined. In particular, the embodiments described herein can automatically (i.e., without user intervention) determine which tests are included in an experiment and when the experiment is complete.

One embodiment relates to a computer-implemented method for determining composition and completion of an experiment. The method includes determining one or more characteristics of data acquired during the experiment. The characteristic(s) may include, for example, number of events detected and counted for a test ("test count" or "event count"), coefficient of variation (CV), standard deviation, etc., or some combination thereof. The one or more characteristics may be determined intermittently or continuously during the experiment. For example, the characteristic(s) may be determined at predetermined intervals during the experiment. The predetermined intervals may be determined before the method is performed and/or may be selected by a user. In addition, the method may include automatically determining the predetermined intervals based on information about the experiment or the measurement system. Furthermore, the method may include altering the predetermined intervals dynamically based on the characteristic(s) of the data. For example, as the characteristic(s) approach the threshold values, the characteristic(s) may be determined more frequently (i.e., at shorter predetermined intervals) such that the completion of the experiment may be determined more accurately and more quickly. The method may determine the characteristic(s) continuously by determining the characteristic(s) after each event has been detected or data for each event has been acquired by the measurement system.

The method also includes determining if the experiment is completed based on the one or more characteristics. For example, the method may include determining if the experiment is complete by comparing the one or more characteristics of the acquired data to a predetermined threshold value for the one or more characteristics. If more than one characteristic is used in the method, each characteristic may be compared to a predetermined threshold value defined specifically for that characteristic. These steps may be performed as described further herein. In addition, this embodiment of the method may include any other step(s) of any other method(s) described herein.

The experiment may include one or more measurements of particles that can be used to determine one or more characteristics of the particles such as numerical values representing the magnitude of fluorescence emission of the particles at multiple detection wavelengths. Subsequent processing of the one or more characteristics of the particles such as using one or more of the numerical values to determine a token ID representing the multiplex subset to which the particles belong and/or a reporter value representing a presence and/or a quantity of analyte bound to the surface of the particles can be performed according to the methods described in U.S. Pat. Nos. 5,736,330 to Fulton, 5,981,180 to Chandler et al., 6,449,562 to Chandler et al., 6,524,793 to Chandler et al., 6,592,822 to Chandler, and 6,939,720 to Chandler et al., which are incorporated by reference as if fully set forth herein. In one example, techniques described in U.S. Pat. No. 5,981,180 to Chandler et al. may be used with the fluorescent measurements described herein in a multiplexing scheme in which the particles are classified into subsets for analysis of multiple analytes in a single sample.

It is noted, however, that the methods and systems described herein can be used for data that is acquired or generated in any manner known in the art. For example, the data may be acquired using a singleplexing scheme, an ELISA reader, or any other assay or test known in the art.

When examining multiple assay tests simultaneously (i.e., in a single experiment), it is often necessary to indicate the tests included in the experiment before the experiment is performed and to define parameters of the experiment that can be used to determine when the experiment is complete. The embodiments described herein eliminate the need to indicate the individual tests before the experiment and can be used to determine or provide one or more parameters used to indicate when the experiment is complete. It is noted that the methods and systems described herein can be used for any multiplex assay test system using any manner of defining tests known in the art (i.e., by fluorescent measurement, size measurement, etc.).

Instead of indicating the tests before the experiment, in embodiments described herein, all tests are initially assumed to be included in the experiment. During, or after the experiment is complete, the method includes applying an algorithm to the data acquired during the experiment and determining the tests that are actually part of the experiment. These steps may be performed automatically. The algorithm can be used to apply one or more threshold criteria to the data to determine the subset of tests that are actually included in the experiment. In addition, during the experiment, the method not only determines the tests included in the experiment, but also determines when the experiment is complete. For instance, in bead-based analysis systems, without the embodiments described herein, a typical test is indicated ahead of time (e.g., by a user) and a minimum number of test events is requested (e.g., by a user). In one particular example, 100 events for each test may be specified in order for the experimental results to be considered valid. For such an example, only when the method has determined that the measurement subsystem being used to perform the experiment has measured 100 or more events of the previously indicated test is the experiment determined to be complete.

With the embodiments described herein, the method assumes that all possible tests are requested and determines the actual tests included in the experiment and the progress of the experiment (e.g., automatically). The method may use a predetermined threshold value and a predetermined event number (both of which may be designated by a user) to determine which tests are included and when the experiment is complete. For example, as the experiment proceeds, the method may include monitoring the number of events detected for all tests and comparing the number of events to the predetermined event numbers and threshold values to determine if the experiment is complete.

In one particular example, if the predetermined threshold value is 50% and the predetermined minimum number of events is 100, the method would allow the experiment to continue until one or more of the tests (the tests actually present in the experiment) have event counts of 100 (or greater) and would terminate the experiment only when all other tests have received less than 50% of the predetermined number of events. In other words, the method may determine that the experiment is complete when tests not actually included in the experiment have 50 event counts or less (most likely due to excessive system noise, misidentification, or sample carryover). Once an event count of 100 (or greater) has been detected for one or more tests, and all other possible tests have counts less than 50, the method determines that the experiment is complete and may record results only for tests with event counts equal to or greater than 100.

The predetermined event count may vary depending on, for example, characteristics of the experiment such as the estimated number of events needed to acquire data having an acceptable CV and the maximum number of events that can be detected for any particular test. The threshold value may vary depending on, for example, the estimated noise in data acquired by the system used to perform the experiment, the uniformity of the sample, and the probability that an event will be assigned to the incorrect test.

Without the embodiments described herein, if all tests are assumed to be part of the experiment, a measurement system being used to perform the experiment would continue to collect data for a sample until at least 100 event counts have been detected for all possible tests, which is a time consuming and fruitless activity because not all tests are present and therefore would not reach a count of 100. This fruitless activity results in increased analysis time and reported data for tests that are not actually part of the experiment (such as test events resulting from system noise as mentioned above). The embodiments described herein can, therefore, be used to reduce analysis time and the amount of reported data that must be processed to determine results of the experiment.

The method embodiments described herein have a number of additional advantages over other methods for performing experiments. For example, selecting the various tests that are part of a particular experiment from all possible tests within a multiplex test analysis is time consuming, can lead to errors, and obligates the user to know ahead of time which tests are to be included. By utilizing the embodiments described herein, the user is not required to identify all of the tests included in the experiment and can proceed with experimentation more quickly and more accurately. In addition, as the number of possible tests that can be performed by a multiplex test analysis system expands, it is highly desirable to allow the system to determine which tests are actually part of a particular experiment. For example, if a system is capable of simultaneously analyzing 1,000 tests as part of a single experiment, but a subset of only 650 tests is actually being utilized in a particular experiment, the method embodiments described herein eliminate the need and time to manually indicate only the 650 tests that are part of the experiment.

The method embodiments described herein can also be used to more easily allow a user to specifically preclude certain tests for which experiment results must not be revealed (a process known as masking) for designated samples but which are actually present in the experiment and are to be reported for all other samples. It is often a less labor intensive process to select for preclusion only the few tests from all possible tests that must be masked, rather than selecting all of the tests present in most samples and not the few tests for particular samples that need to be masked. By selecting only precluded tests for certain samples, revealing data for only particular tests allowed to be reported for all samples is made possible in a more efficient manner.

Furthermore, users of multiplex systems sometimes use different tests for different samples within a single experiment. Without the embodiments described herein, users are required to: 1) identify all of the tests included in the entire experiment across all samples, regardless of which subsets of tests are actually used for particular samples; and 2) designate a "total count" threshold so that the results for each test are permitted to be recorded regardless of whether the tests are used for each sample. If the embodiments described herein are utilized, requiring the user to indicate all of the tests included in the entire experiment and further requiring the user to select a "total count" for the experiment can be eliminated.

Other experiment criteria in addition to and dependent on the test count criteria described above can be used in the embodiments described herein to further refine the experiment. For instance, a secondary threshold may be defined and used by the method that further defines when the experiment is completed. The secondary threshold may be a threshold relating to the standard deviation or CV for the data acquired during the experiment. For example, if a CV of 10% is defined as an additional threshold that is used in combination with a test count threshold of 100 and a count threshold of 50%, the experiment would be allowed to continue until the event count for at least one test is 100 (or greater), events counts for all other possible tests are less than 50, and the data acquired for tests with counts of 100 or greater has CV values of less than 10%. This embodiment can be used to define parameters of the experiment using any number of additional thresholds in any combination (e.g., using both a CV threshold and a standard deviation threshold).

Some currently used methods employ a subset of the criteria described above (e.g., only CV) to define experiment stop criteria for measurement systems such as radioactivity counters. Such methods would, therefore, continue the experiment and only provide a final result after an acceptable CV for the data has been achieved. However, the embodiments described herein use such a threshold as secondary stop criteria that is dependent on whether or not a threshold for the primary stop criteria has been exceeded. As described above, the primary stop criteria relates to the identification of the tests themselves in an experiment being performed by a multiplexed system.

Utilizing the additional thresholds described above provides advantages in addition to those described above. For example, with the addition of secondary thresholds, the quality of the data acquired during the experiment can be specified to ensure that the acquired data is acceptable. In contrast, if test count alone is used to determine when an experiment is completed, the quality of the data at the time the experiment is determined to be complete may be unacceptable. The method embodiments described herein, therefore, advantageously allow additional thresholds to be defined and used in order to extend the experiment to ensure that results for the identified tests have been acquired with acceptable characteristics.

Moreover, although a number of different measurement subsystems are described further herein that can be used with (or can be used to perform) the embodiments described herein, it is to be understood that the embodiments described herein can be used in or with any other measurement subsystems that are commercially available from Luminex Corporation and any other commercially available measurement subsystems that have multiplex testing capability. The benefits of the embodiments described herein also become more advantageous when the multiplexing capability of the measurement subsystem is increased. The embodiments described herein can also be used in combination with methods and systems for automatically determining assay type such as those described in U.S. Patent Application Ser. No. 60/732,535 filed on Nov. 2, 2005 by Ward, which is incorporated by reference as if fully set forth herein. The methods described herein can include any step(s) of any method(s) described in this patent application, and the systems described herein can be further configured as described in this patent application.

A simulation of an experiment at different time points during data collection is described further below to demonstrate how the above methods can be performed and is provided to further understanding of the embodiments described herein. The simulation results described herein are not to be construed as limiting embodiments of the present invention.

The first simulation described herein is for a method that utilizes only the test identification and stop criteria related to test count described above to determine when the experiment is complete and which tests are included in the experiment. The predetermined event count (or number of events) is 100, and the count threshold is 50%. Table 1 represents simulated data for a multiplex experiment.

TABLE 1

| Time point | Number of events recorded at specified Time Point ||||||| 
|---|---|---|---|---|---|---|---|
| | Test 1 | Test 2 | Test 3 | Test 4 | Test 5 | Test 6 | Test 7 |
| 1 | 18 | 25 | 11 | 11 | 22 | 24 | 3 |
| 2 | 35 | 48 | 35 | 26 | 44 | 41 | 6 |
| 3 | 63 | 83 | 59 | 57 | 69 | 67 | 9 |
| 4 | 85 | 106 | 81 | 83 | 89 | 94 | 12 |
| 5 | 100 | 121 | 100 | 105 | 112 | 113 | 15 |

Tests 1-6 in Table 1 represent tests actually included in the experiment. Although six tests are included in this example of an experiment, it is to be understood that an actual experiment may include any number of tests (i.e., one or more tests). Test 7 represents a test that is not included in the experiment, but for which event counts were detected due to excessive system noise, misidentification, or sample carryover. It is noted that simulated results for only Test 7, which is not actually included in the experiment, are shown in this table but all other tests are initially assumed to be part of the experiment by the method. Therefore, the method embodiments described herein would monitor the event counts detected for all possible tests.

As shown in Table 1, at Time Points 1-3, the event counts for none of the tests are greater than 100 so the method determines that the experiment should continue. At Time Point 4, the event count for Test 2 is greater than 100 but because the event counts for other tests (Tests 1 and 3-6) are within 50% of the predetermined event count, the method determines that the experiment should continue. At Time Point 5, the event counts for Tests 1-6 are equal to or greater than 100, and the event count for Test 7 (not actually present in the experiment) is less than 50% of the predetermined event count. Therefore, the method determines (e.g., automatically) that the experiment is complete, and the method would stop experimentation with the sample and may report results for only Tests 1-6.

Turning now to the drawings, it is noted that the figures are not drawn to scale. In particular, the scale of some of the elements of the figures is greatly exaggerated to emphasize characteristics of the elements.

FIGS. 1-5 are representative graphical displays of the five time points during the simulated experiment described above at which a characteristic of the experiment is determined. The characteristic that is determined is the number of events detected at specific time points for different tests. The data shown in FIGS. 1-5 at Time Points 1-5, respectively, corresponds to the data shown in Table 1 at the same Time Points. In FIGS. 1-5, the seven tests (numbered 1 to 7 from the bottom row left to right, then the top row left to right) are indicated by the white regions in the graphs only for clarification in the simulation. In the implementation of the embodiments described herein, no tests are indicated prior to the experiment.

Figure 2:
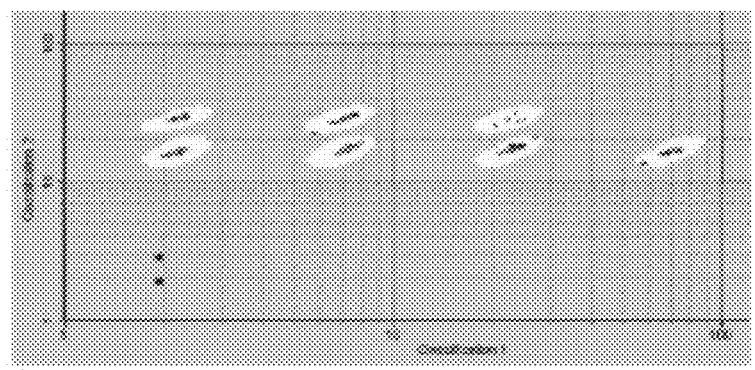
Figure 3:
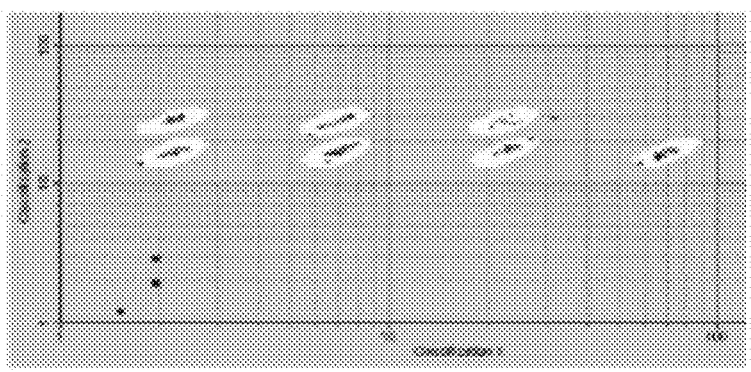

FIG. 1 illustrates the number of events detected for each test at Time Point 1. At Time Point 1, event counts of 100 or greater have not been detected for any of the tests. Therefore, the method determines that the experiment is not complete at Time Point 1, and the experiment continues. FIG. 2 illustrates the number of events detected for Tests 1-7 at Time Point 2. At Time Point 2, the event count detected for each of Tests 1-7 is not 100 or greater. Therefore, the method determines that the experiment is not complete at Time Point 2, and the experiment continues. FIG. 3 illustrates the number of events detected for Tests 1-7 at Time Point 3. At Time Point 3, the event count detected for none of the tests is 100 or greater. Therefore, the method determines that the experiment is not complete at Time Point 3, and the experiment continues.

Figure 4:
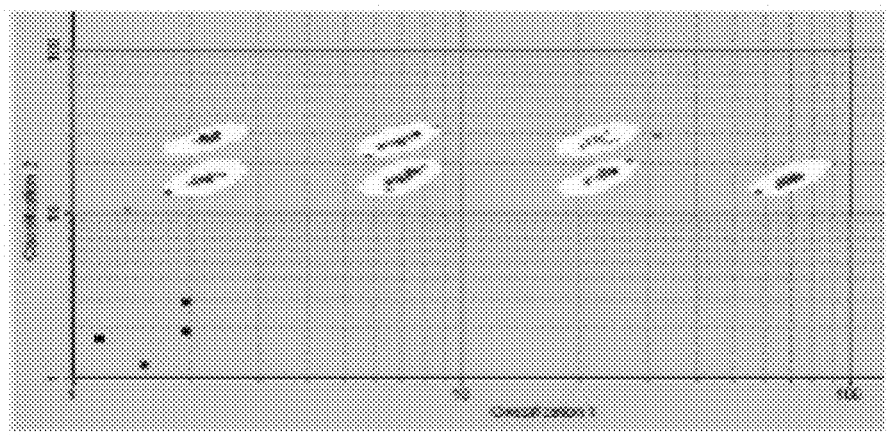
Figure 5:
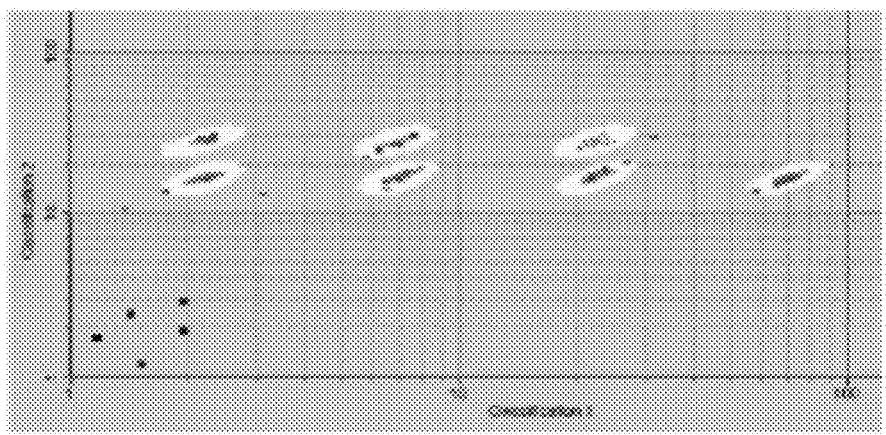

FIG. 4 illustrates the number of events detected for each of the tests at Time Point 4. At Time Point 4, the event count for Test 2 is greater than 100. However, the event counts for other tests are within 50% of the predetermined event count at Time Point 4. Therefore, the method determines that the experiment is not complete at Time Point 4, and the experiment continues. FIG. 5 illustrates the number of events detected for each of the tests at Time Point 5. At Time Point 5, the event counts for Tests 1-6 are greater than 100, and Test 7 (not actually present in the experiment) has an event count less than 50% of 100. Therefore, the method determines that the experiment is complete at Time Point 5, and the method will stop the experiment with the sample (e.g., by controlling one or more parameters of a measurement subsystem or a system that includes a measurement subsystem being used to perform the experiment) and may report results for only Tests 1-6.

The second simulation described herein illustrates a method that uses an additional stop criteria threshold based on the CV of the data acquired during an experiment, which is used in addition to and is dependent on the test identification and stop criteria related to test count described further above. In this simulation, the selected event count is 100, the count threshold is 50%, and the CV threshold is 10%. The following tables represent simulated data for a multiplex experiment. Tests 1-6 represent tests actually included in the experiment. However, the multiplex experiment may include any number of tests (i.e., one or more tests). Test 7 represents a test that is not included in the experiment, but for which event counts are detected due to excessive system noise, misidentification, or sample carryover. It is noted that only Test 7, which is not included in the experiment, is shown in this simulation, but all other tests are initially assumed to be part of the experiment and data acquired during the experiment for all possible tests would be considered by the method embodiments described herein.

TABLE 2

| Time Point 1 | Test 1 | Test 2 | Test 3 | Test 4 | Test 5 | Test 6 | Test 7 |
|---|---|---|---|---|---|---|---|
| Count | 18 | 25 | 11 | 11 | 22 | 24 | 3 |
| CV | 42 | 60 | 42 | 31 | 53 | 49 | 79 |

As shown in Table 2, at Time Point 1, event counts of 100 or greater have not been detected for any of the tests, so the method determines that the experiment is not complete, and the experiment is allowed to continue.

TABLE 3

| Time Point 2 | Test 1 | Test 2 | Test 3 | Test 4 | Test 5 | Test 6 | Test 7 |
|---|---|---|---|---|---|---|---|
| Count | 35 | 48 | 35 | 26 | 44 | 41 | 6 |
| CV | 34 | 46 | 34 | 25 | 42 | 39 | 71 |

As shown in Table 3, at Time Point 2, event counts of 100 or greater have not been detected for any of the tests, so the method determines that the experiment is not complete, and the experiment is allowed to continue.

TABLE 4

| Time Point 3 | Test 1 | Test 2 | Test 3 | Test 4 | Test 5 | Test 6 | Test 7 |
|---|---|---|---|---|---|---|---|
| Count | 63 | 83 | 59 | 57 | 69 | 67 | 9 |
| CV | 20 | 29 | 20 | 15 | 25 | 24 | 68 |

As shown in Table 4, at Time Point 3, event counts of 100 or greater have not been detected for any of the tests, so the method determines that the experiment is not complete, and the experiment is allowed to continue.

TABLE 5

| Time Point 4 | Test 1 | Test 2 | Test 3 | Test 4 | Test 5 | Test 6 | Test 7 |
|---|---|---|---|---|---|---|---|
| Count | 85 | 106 | 81 | 83 | 89 | 94 | 12 |
| CV | 12 | 17 | 12 | 9 | 15 | 14 | 67 |

As shown in Table 5, at Time Point 4, an event count greater than 100 is detected for Test 2, but because event counts for other tests are within 50% of the predetermined event count, the method determines that the experiment is not complete, and the experiment is allowed to continue.

TABLE 6

| Time Point 5 | Test 1 | Test 2 | Test 3 | Test 4 | Test 5 | Test 6 | Test 7 |
|---|---|---|---|---|---|---|---|
| Count | 100 | 121 | 100 | 105 | 112 | 113 | 15 |
| CV | 7 | 11 | 7 | 5 | 9 | 9 | 65 |

As shown in Table 6, at Time Point 5, the first criteria based on event count has been satisfied since event counts equal to or greater than 100 have been detected for Tests 1-6, and Test 7 (not actually present in the experiment) has an event count of less than 50% of the predetermined event count. However, because the data acquired for Test 2 does not have a CV less than 10, the method determines that the experiment is not complete, and the experiment is allowed to continue.

TABLE 7

| Time Point 6 | Test 1 | Test 2 | Test 3 | Test 4 | Test 5 | Test 6 | Test 7 |
|---|---|---|---|---|---|---|---|
| Count | 120 | 145 | 122 | 126 | 134 | 136 | 18 |
| CV | 4 | 9 | 4 | 3 | 5 | 5 | 64 |

As shown in Table 7, at Time Point 6, the first criteria has been satisfied since an event count equal to or greater than 100 has been detected for Tests 1-6, and Test 7 (not actually present in the experiment) has an event count less than 50% of the predetermined event count. In addition, the data acquired for all tests that have satisfied the first criteria (Tests 1-6) has a CV of less than 10. Therefore, Tests 1-6 have satisfied both the first and second criteria. As such, at Time Point 6, the method determines that the experiment is complete, and the method stops the experiment (e.g., by controlling a measurement subsystem or a system that includes a measurement subsystem used to perform the experiment) and may report the results for only Tests 1-6 (i.e., only results for tests actually included in the experiment).

Figure 6:
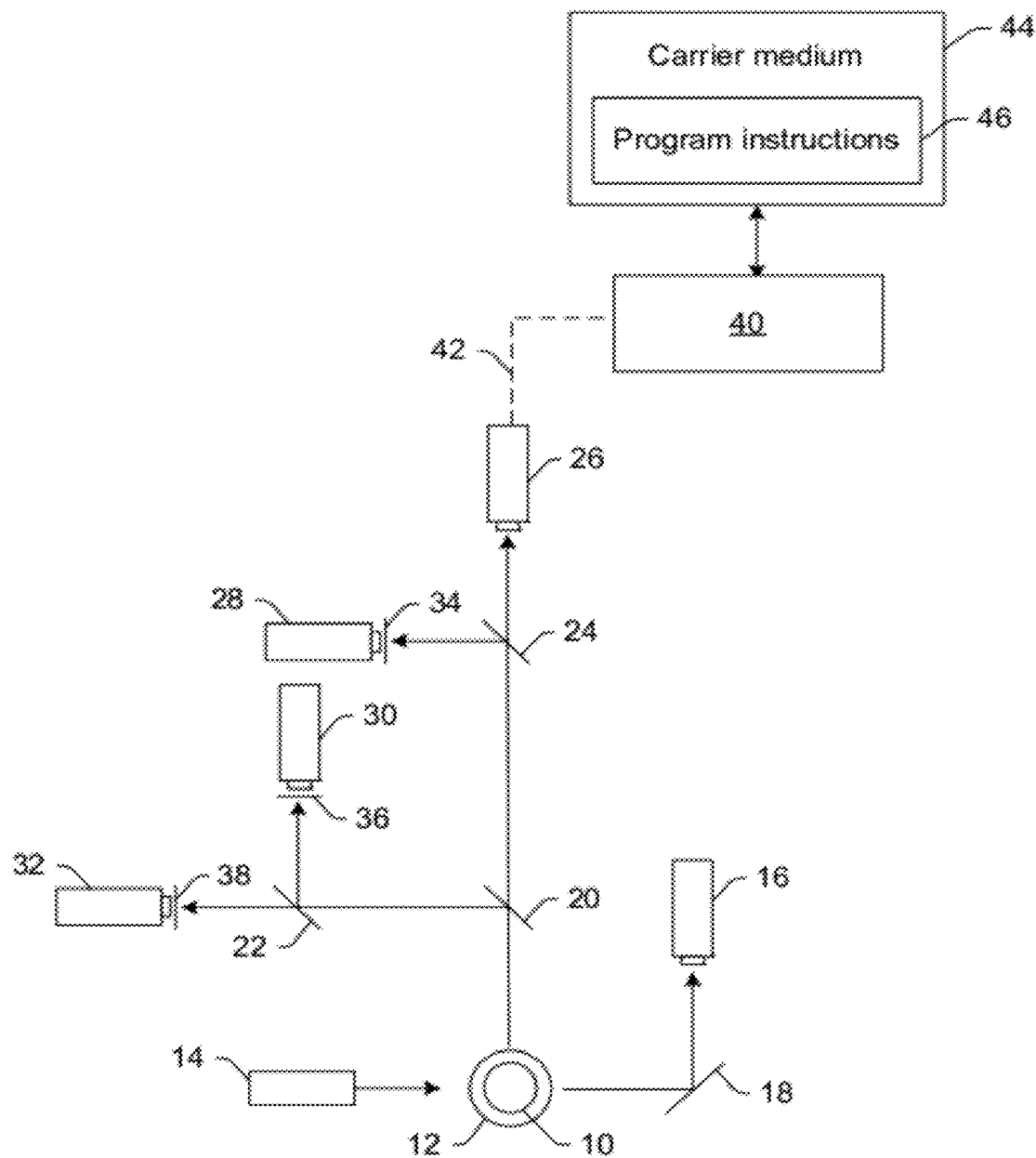
FIGS. 6-7 are schematic diagrams illustrating a cross-sectional view of various embodiments of a system configured to perform an experiment and to determine composition and completion of an experiment.

Another embodiment relates to carrier medium 44 shown in FIG. 6 that includes program instructions 46 executable on a computer system (e.g., processor 40) for performing a computer-implemented method for determining composition and completion of an experiment. The computer-implemented method includes determining one or more characteristics of data acquired during the experiment. The method also includes determining if the experiment is completed based on the one or more characteristics. These steps may be performed as described herein. The computer-implemented method for which the program instructions are executable may include any other step(s) of any other method(s) described herein.

Program instructions 46 implementing methods such as those described herein may be transmitted over or stored on the carrier medium. The carrier medium may be a transmission medium such as a wire, cable, or wireless transmission link. The carrier medium may also be a storage medium such as a read-only memory, a random access memory, a magnetic or optical disk, or a magnetic tape.

Processor 40 may be a processor such as those commonly included in a typical personal computer, mainframe computer system, workstation, etc. In general, the term "computer system" may be broadly defined to encompass any device having one or more processors, which executes instructions from a memory medium. The processor may be implemented using any other appropriate functional hardware. For example, the processor may include a digital signal processor (DSP) with a fixed program in firmware, a field programmable gate array (FPGA), or other programmable logic device (PLD) employing sequential logic "written" in a high level programming language such as very high speed integrated circuits (VHSIC) hardware description language (VHDL). In another example, program instructions 46 executable on processor 40 to perform one or more steps of the computer-implemented methods described herein may be coded in a high level language such as C#, with sections in C++ as appropriate, ActiveX controls, JavaBeans, Microsoft Foundation Classes ("MFC"), or other technologies or methodologies, as desired. The program instructions may be implemented in any of various ways, including procedure-based techniques, component-based techniques, and/or object-oriented techniques, among others.

FIG. 6 also illustrates one embodiment of a system configured to determine composition and completion of an experiment. In one embodiment, the system includes processor 40 configured to determine one or more characteristics of data acquired during the experiment and to determine the composition of the experiment and if the experiment is completed based on the one or more characteristics. Processor 40 may be configured to perform these steps according to any of the embodiments described herein. This embodiment of the system and processor 40 may be further configured as described herein.

FIG. 6 further illustrates one embodiment of a system configured to perform an experiment. The system includes a measurement subsystem configured to acquire data during the experiment. The system also includes processor 40 configured to determine one or more characteristics of the data during the experiment and to determine the composition of the experiment and if the experiment is completed based on the one or more characteristics. Processor 40 may be further configured as described herein.

In FIG. 6, the measurement subsystem is shown along a plane through the cross-section of cuvette 12 through which microspheres 10 flow. In one example, the cuvette may be a standard quartz or fused-silica cuvette such as that used in standard flow cytometers. Any other suitable type of viewing or delivery chamber, however, may also be used to deliver the sample for analysis.

The measurement subsystem includes light source 14. Light source 14 may include any appropriate light source known in the art such as a laser. The light source may be configured to emit light having one or more wavelengths such as blue light or green light. Light source 14 may be configured to illuminate the microspheres as they flow through the cuvette. The illumination may cause the microspheres to emit fluorescent light having one or more wavelengths or wavelength bands. In some embodiments, the measurement subsystem may include one or more lenses (not shown) configured to focus light from the light source onto the microspheres or the flowpath. The measurement subsystem may also include more than one light source. In one embodiment, the light sources may be configured to illuminate the microspheres with light having different wavelengths or wavelength bands (e.g., blue light and green light). In some embodiments, the light sources may be configured to illuminate the microspheres at different directions.

The measurement subsystem also includes detection system 16 and folding mirror 18. Light scattered forwardly from the microspheres may be directed to detection system 16 by folding mirror 18 or another suitable light directing component. Alternatively, detection system 16 may be placed directly in the path of the forwardly scattered light. In this manner, the folding mirror or other light directing components may not be included in the measurement subsystem. In one embodiment, the forwardly scattered light may be light scattered by the microspheres at an angle of about 180° from the direction of illumination by light source 14, as shown in FIG. 6. The angle of the forwardly scattered light may not be exactly 180° from the direction of illumination such that incident light from the light source may not impinge upon the photosensitive surface of the detection system. For example, the forwardly scattered light may be light scattered by the microspheres at angles less than or greater than 180° from the direction of illumination (e.g., light scattered at an angle of about 170°, about 175°, about 185°, or about) 190°.

Light scattered by the microspheres at an angle of about 90° from the direction of illumination may also be collected by the measurement subsystem. In one embodiment, this scattered light may be separated into more than one beam of light by one or more beamsplitters or dichroic mirrors included in the measurement subsystem. For example, light scattered at an angle of about 90° to the direction of illumination may be separated into two different beams of light by beamsplitter 20. The two different beams of light may be separated again by beamsplitters 22 and 24 to produce four different beams of light. Each of the beams of light may be directed to a different detection system, which may include one or more detectors. For example, one of the four beams of light may be directed to detection system 26 of the measurement subsystem. Detection system 26 may be configured to detect light scattered by the microspheres.

Scattered light detected by detection system 16 and/or detection system 26 may generally be proportional to the volume of the particles that are illuminated by the light source. Therefore, output signals of detection system 16 and/or output signals of detection system 26 may be used to determine a diameter of the particles that are in the illumination zone or detection window. In addition, the output signals of detection system 16 and/or detection system 26 may be used to identify more than one particle that are stuck together or that are passing through the illumination zone at approximately the same time. Therefore, such particles may be distinguished from other sample microspheres and calibration microspheres. Furthermore, the output signals of detection system 16 and/or detection system 26 may be used to distinguish between sample microspheres and calibration microspheres based on size.

The measurement subsystem also includes detection systems 28, 30, and 32. The other three beams of light may be directed to detection systems 28, 30, and 32. Detection systems 28, 30, and 32 may be configured to detect fluorescence emitted by the microspheres. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence.

The measurement subsystem may also include spectral filters 34, 36, and 38. In some embodiments, spectral filters 34, 36, and 38 may be coupled to detection systems 28, 30, and 32, respectively. The spectral filters may be configured to block fluorescence of wavelengths other than that or those which the detection systems are configured to detect. In addition, one or more lenses (not shown) may be optically coupled to each of the detection systems. The lenses may be configured to focus the scattered light or emitted fluorescence onto a photosensitive surface of the detectors.

The detector's output current is proportional to the fluorescent light impinging on it and results in a current pulse. The current pulse may be converted to a voltage pulse, low pass filtered, and then digitized by an A/D converter. Processor 40 such as a DSP integrates the area under the pulse to provide a number which represents the magnitude of the fluorescence. In addition, the processor may perform additional functions described herein. As shown in FIG. 6, processor 40 may be coupled to detector 26 via transmission medium 42. Processor 40 may also be coupled to detector 26 indirectly via transmission medium 42 and one or more other components (not shown) such as the A/D converter. The processor may be coupled to other detectors of the system in a similar manner.

In some embodiments, the output signals generated from fluorescence emitted by the microspheres may be used to determine an identity of the microspheres and information about a reaction taking or taken place on the surface of the microspheres. For example, output signals of two of the detection systems may be used to determine an identity of the microspheres, and output signals of the other detection system may be used to determine a reaction taking or taken place on the surface of the microspheres. Therefore, the selection of the detectors and the spectral filters may vary depending on the type of dyes incorporated into or bound to the microspheres and/or the reaction being measured (i.e., the dye(s) incorporated into or bound to the reactants involved in the reaction).

The detection systems that are used to determine an identity of the sample microspheres (e.g., detection systems 28 and 30) may be APDs, a PMT, or another photodetector. The detection system that is used to identify a reaction taken or taking place on the surface of the microspheres (e.g., detection system 32) may be a PMT, an APD, or another form of photodetector. The detectors and the measurement subsystem may be further configured as described herein.

Although the measurement subsystem of FIG. 6 is shown to include two detection systems having two different detection windows for distinguishing between microspheres having different dye characteristics, it is to be understood that the measurement subsystem may include more than two such detection windows (i.e., 3 detection windows, 4 detection windows, etc.). In such embodiments, the measurement subsystem may include additional beamsplitters and additional detection systems having other detection windows. In addition, spectral filters and/or lenses may be coupled to each of the additional detection systems.

In another embodiment, the measurement subsystem may include two or more detection systems configured to distinguish between different materials that are reacted on the surface of the microspheres. The different reactant materials may have dye characteristics that are different than the dye characteristics of the microspheres.

Additional examples of measurement subsystems that may be included in the systems described herein are illustrated in U.S. Pat. Nos. 5,981,180 to Chandler et al., 6,046,807 to Chandler, 6,139,800 to Chandler, 6,366,354 to Chandler, 6,411,904 to Chandler, 6,449,562 to Chandler et al., and 6,524,793 to Chandler et al., which are incorporated by reference as if fully set forth herein. The measurement subsystem described herein may also be further configured as described in these patents. The system shown in FIG. 6 has all of the advantages of other embodiments described herein.

Figure 7:
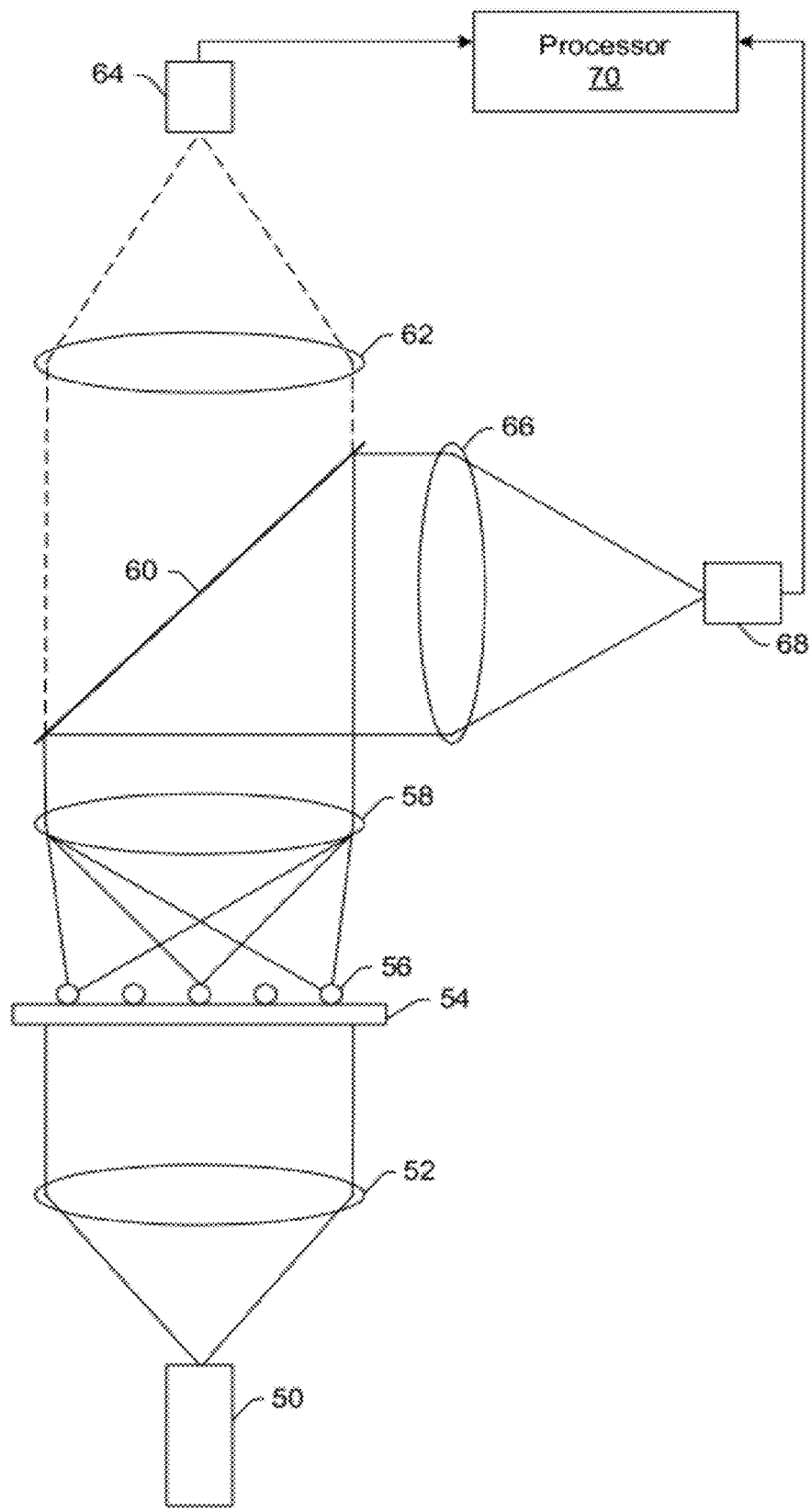

FIG. 7 illustrates another embodiment of a system configured to perform an experiment. The system includes a measurement subsystem configured to acquire data during the experiment. The system also includes a processor configured to determine one or more characteristics of the data during the experiment and to determine the composition of the experiment and if the experiment is completed based on the one or more characteristics. The processor may be configured to perform these steps as described further herein.

The system shown in FIG. 7 may be used in applications such as multi-analyte measurement of particles. The measurement subsystem includes an imaging subsystem that includes light source 50. Light source 50 may include one or more light sources such as light emitting diodes (LED), lasers, arc lamps, incandescent lamps, or any other suitable light sources known in the art. In addition, or alternatively, the imaging subsystem may include more than one light source (not shown), each of which is configured to generate light of at least one wavelength or at least one wavelength band. One example of an appropriate combination of light sources for use in the system shown in FIG. 7 includes, but is not limited to, two or more LEDs.

Light from more than one light source may be combined into a common illumination path by a beamsplitter (not shown) or any other suitable optical element known in the art such that light from the light sources may be directed to the particles simultaneously. Alternatively, the imaging subsystem may include an optical element (not shown) such as a reflecting mirror and a device (not shown) configured to move the optical element into and out of the illumination path depending on which light source is used to illuminate the particles. In this manner, the light sources may be used to sequentially illuminate the particles with different wavelengths or wavelength bands of light. The light source(s) may also illuminate the substrate from above, rather than from below the substrate (not shown).

The light source(s) may be selected to provide light at wavelength(s) or wavelength band(s) that will cause the particles or material coupled thereto to emit fluorescence. For instance, the wavelength(s) or wavelength band(s) may be selected to excite fluorescent dyes or other fluorescent materials incorporated into the particles and/or coupled to a surface of the particles. In this manner, the wavelength(s) or wavelength band(s) may be selected such that the particles emit fluorescence that is used for classification of the particles. In addition, the wavelength(s) or wavelength band(s) may be selected to excite fluorescent dyes or other fluorescent materials coupled to the particles via a reagent on the surface of the particles. As such, the wavelength(s) or wavelength band(s) may be selected such that the particles emit fluorescence that is used to detect and/or quantify reaction(s) that have taken place on the surface of the particles.

As shown in FIG. 7, the imaging subsystem may include optical element 52 that is configured to direct light from light source 50 to substrate 54 on which particles 56 are immobilized. In one example, optical element 52 may be a collimating lens. However, optical element 52 may include any other appropriate optical element that can be used to image light from light source 50 onto substrate 54. In addition, although the optical element is shown in FIG. 7 as a single optical element, it is to be understood that optical element 52 may include more than one refractive element. Furthermore, although optical element 52 is shown in FIG. 7 as a refractive optical element, it is to be understood that one or more reflective and/or diffractive optical elements may be used (possibly in combination with one or more refractive optical elements) to image light from light source 50 onto substrate 54. Although the system is shown in FIG. 7 as being configured to image light from light source 50 onto substrate 54 at a substantially normal angle of incidence, it is to be understood that the system may be configured to image the light onto the substrate at an oblique angle of incidence.

Particles 56 may include any of the particles described above. Substrate 54 may include any appropriate substrate known in the art. The particles immobilized on substrate 54 may be disposed in an imaging chamber (not shown) or any other device for maintaining a position of substrate 54 and particles 56 immobilized thereon with respect to the imaging subsystem. The device for maintaining a position of substrate 54 may also be configured to alter a position of the substrate (e.g., to focus the imaging subsystem onto the substrate) prior to imaging.

Immobilization of the particles on the substrate may be performed using magnetic attraction, a vacuum filter plate, or any other appropriate method known in the art. Examples of methods and systems for positioning microspheres for imaging are illustrated in U.S. patent application Ser. No. 11/270,786 to Pempsell filed Nov. 9, 2005, which is incorporated by reference as if fully set forth herein. The particle immobilization method itself is not particularly important to the methods and systems described herein. However, the particles are preferably immobilized such that the particles do no move perceptibly during the detector integration period, which may be multiple seconds long.

As shown in FIG. 7, the imaging subsystem may include optical element 58 and beamsplitter 60. Optical element 58 is configured to collect and collimate light from substrate 54 and particles 56 immobilized thereon and to direct the light to beamsplitter 60. Optical element 58 may be further configured as described above with respect to optical element 52. Beamsplitter 60 may include any appropriate beamsplitter known in the art. Beamsplitter 60 may be configured to direct light from optical element 58 to different detectors based on the wavelength of the light. For example, light having a first wavelength or wavelength band may be transmitted by beamsplitter 60, and light having a second wavelength or wavelength band different than the first may be reflected by beamsplitter 60.

The imaging subsystem may also include optical element 62 and detector 64. Light transmitted by beamsplitter 60 may be directed to optical element 62. Optical element 62 is configured to focus the light transmitted by the beamsplitter onto detector 64. The imaging subsystem may further include optical element 66 and detector 68. Light reflected by beamsplitter 60 may be directed to optical element 66. Optical element 66 is configured to focus the light reflected by the beamsplitter onto detector 68. Optical elements 62 and 66 may be configured as described above with respect to optical element 52.

Detectors 64 and 68 may include, for example, charge coupled device (CCD) detectors or any other suitable imaging detectors known in the art such as CMOS detectors, two-dimensional arrays of photosensitive elements, time delay integration (TDI) detectors, etc. In some embodiments, a detector such as a two-dimensional CCD imaging array may be used to acquire an image of substantially an entire substrate or of all particles immobilized on a substrate simultaneously. In this manner, all photons from the illuminated area of the substrate may be collected simultaneously thereby eliminating error due to a sampling aperture used in other currently available systems that include a photomultiplier tube (PMT) and scanning device. In addition, the number of detectors included in the system may be equal to the number of wavelengths or wavelength bands of interest such that each detector is used to generate images at one of the wavelengths or wavelength bands.

Each of the images generated by the detectors may be spectrally filtered using an optical bandpass element (not shown) or any other suitable optical element known in the art, which is disposed in the light path from the beamsplitter to the detectors. A different filter "band" may be used for each captured image. The detection wavelength center and width for each wavelength or wavelength band at which an image is acquired may be matched to the fluorescent emission of interest, whether it is used for particle classification or the reporter signal.

In this manner, the imaging subsystem of the system shown in FIG. 7 is configured to generate multiple images at different wavelengths or wavelength bands simultaneously. Although the imaging subsystem shown in FIG. 7 includes two detectors, it is to be understood that the imaging subsystem may include more than two detectors (e.g., three detectors, four detectors, etc.). As described above, each of the detectors may be configured to generate images at different wavelengths or wavelength bands simultaneously by including one or more optical elements for directing light at different wavelengths or wavelength bands to the different detectors simultaneously.

Although the imaging subsystem is shown in FIG. 7 to include multiple detectors, it is to be understood that the imaging subsystem may include a single detector. The single detector may be used to generate multiple images at multiple wavelengths or wavelength bands sequentially. For example, light of different wavelengths or wavelength bands may be directed to the substrate sequentially, and different images may be generated during illumination of the substrate with each of the different wavelengths or wavelength bands. In another example, different filters for selecting the wavelength or wavelength bands of light directed to the single detector may be altered (e.g., by moving the different filters into and out of the imaging path) to generate images at different wavelengths or wavelength bands sequentially.

The imaging subsystem shown in FIG. 7 is, therefore, configured to generate a plurality or series of images representing the fluorescent emission of particles 56 at several wavelengths of interest. In addition, the imaging subsystem may be configured to supply a plurality or series of digital images representing the fluorescence emission of the particles to a processor (i.e., a processing engine). In one such embodiment, the system includes processor 70. Processor 70 may be configured to acquire (e.g., receive) image data from detectors 64 and 68. For example, processor 70 may be coupled to detectors 64 and 68 in any suitable manner known in the art (e.g., via transmission media (not shown), each coupling one of the detectors to the processor, via one or more electronic components (not shown) such as analog-to-digital converters, each coupled between one of the detectors and the processor, etc.).

Preferably, processor 70 is configured to process and analyze these images to determine one or more characteristics of particles 56 such as a classification of the particles and information about a reaction taken or taking place on the surface of the particles. The one or more characteristics may be output by the processor in any suitable format such as a data array with an entry for fluorescent magnitude for each particle for each wavelength. Processor 70 may be further configured as described herein. The system shown in FIG. 7 may also be further configured as described herein. The system shown in FIG. 7 has all of the advantages of other embodiments described herein.

It will be appreciated to those skilled in the art having the benefit of this disclosure that this invention is believed to provide methods and systems for determining composition and completion of an experiment. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system for performing multiple assay tests in a single experiment without specifying which assay tests to perform prior to conducting the single experiment, the system comprising:
   a transport mechanism configured to convey a plurality of particles to an examination region;
   one or more light sources for illuminating particles in said examination region;
   a detection system configured for acquiring data from said illumination of particles; and
   a processor coupled to the detection system, wherein said processor includes a storage medium having program instructions, which are executed by the processor for: (i) determining one or more characteristics of the acquired data, (ii) determining which tests are performed in the experiment based on said characteristics, wherein said processor determines which tests are performed in the experiment by associating certain characteristics of the acquired data with certain tests, and determining a certain test is performed in the experiment if a certain characteristic exceeds a threshold, and (iii) determining if the experiment is complete.

2. The system of claim 1, wherein said certain characteristic is an event count of events associated with said certain test.

3. The system of claim 2, wherein said system is a flow cytometer, said particles include fluorescent material, an event is light scattered by a particle, and if the number of events exceed said threshold, the certain test is deemed part of said experiment.

4. The system of claim 1, wherein said processor determines the experiment is complete based on associating certain characteristics with certain tests, and determining if a number of said tests have associated characteristics which exceed a predetermined first parameter.

5. The system of claim 4, including determining if associated characteristics of any tests which are less than said first parameter, are below a second parameter.

6. The system of claim 4, including determining if said associated characteristics of any tests meet defined statistical criteria.

* * * * *